US011642153B2

(12) United States Patent
Pilletere et al.

(10) Patent No.: US 11,642,153 B2
(45) Date of Patent: May 9, 2023

(54) INSTRUMENT SEAL FOR SURGICAL ACCESS ASSEMBLY

(71) Applicant: Covidien LP, Mansfield, MA (US)

(72) Inventors: Roy J. Pilletere, North Haven, CT (US); Garrett P. Ebersole, Hamden, CT (US); Eric Brown, Madison, CT (US); Matthew A. Dinino, Newington, CT (US); Jacob C. Baril, Norwalk, CT (US); Richard C. Hart, Clinton, CT (US); Justin Thomas, New Haven, CT (US); Nicolette R. LaPierre, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 333 days.

(21) Appl. No.: 16/823,503

(22) Filed: Mar. 19, 2020

(65) Prior Publication Data
US 2021/0290266 A1    Sep. 23, 2021

(51) Int. Cl.
*A61B 17/34* (2006.01)

(52) U.S. Cl.
CPC ...... *A61B 17/3462* (2013.01); *A61B 17/3423* (2013.01); *A61B 17/3498* (2013.01); *A61B 2017/3425* (2013.01)

(58) Field of Classification Search
CPC ........ A61B 17/3462; A61B 2017/3464; A61B 17/3423; A61B 17/34–3498
See application file for complete search history.

(56) References Cited

U.S. PATENT DOCUMENTS

| 3,402,710 | A | 9/1968 | Paleschuck |
| 3,495,586 | A | 2/1970 | Regenbogen |
| 4,016,884 | A | 4/1977 | Kwan-Gett |
| 4,112,932 | A | 9/1978 | Chiulli |
| 4,183,357 | A | 1/1980 | Bentley et al. |
| 4,356,826 | A | 11/1982 | Kubota |
| 4,402,683 | A | 9/1983 | Kopman |
| 4,619,643 | A | 10/1986 | Bai |
| 4,653,476 | A | 3/1987 | Bonnet |
| 4,737,148 | A | 4/1988 | Blake |

(Continued)

FOREIGN PATENT DOCUMENTS

| EP | 3219268 A1 | 9/2017 |
| WO | 2012131746 A1 | 10/2012 |
| WO | 2016110720 A1 | 7/2016 |

OTHER PUBLICATIONS

Partial European Search Report dated Jul. 21, 2021 issued in corresponding EP Appln. No. 21163414.2.

(Continued)

*Primary Examiner* — Darwin P Erezo
*Assistant Examiner* — Brigid K Byrd
(74) *Attorney, Agent, or Firm* — Carter, DeLuca & Farrell LLP

(57) ABSTRACT

A surgical access assembly includes a housing, a tubular member, and a valve assembly. The tubular member extends from the housing. The valve assembly is positioned in the housing and includes a centering mechanism, a guard assembly disposed on a first side of the centering mechanism, and an instrument seal disposed on a second side of the centering mechanism. The instrument seal including petals that are arrange in an overlapping arrangement.

17 Claims, 11 Drawing Sheets

(56) References Cited

U.S. PATENT DOCUMENTS

| | | | |
|---|---|---|---|
| 4,863,430 | A | 9/1989 | Klyce et al. |
| 4,863,438 | A | 9/1989 | Gauderer et al. |
| 4,984,564 | A | 1/1991 | Yuen |
| 5,002,557 | A | 3/1991 | Hasson |
| 5,073,169 | A | 12/1991 | Raiken |
| 5,082,005 | A | 1/1992 | Kaldany |
| 5,122,122 | A | 6/1992 | Allgood |
| 5,159,921 | A | 11/1992 | Hoover |
| 5,176,697 | A | 1/1993 | Hasson et al. |
| 5,183,471 | A | 2/1993 | Wilk |
| 5,192,301 | A | 3/1993 | Kamiya et al. |
| 5,209,741 | A | 5/1993 | Spaeth |
| 5,209,754 | A | 5/1993 | Ahluwalia |
| 5,217,466 | A | 6/1993 | Hasson |
| 5,242,409 | A | 9/1993 | Buelna |
| 5,242,415 | A | 9/1993 | Kantrowitz et al. |
| 5,257,973 | A | 11/1993 | Villasuso |
| 5,257,975 | A | 11/1993 | Foshee |
| 5,269,772 | A | 12/1993 | Wilk |
| 5,271,380 | A | 12/1993 | Riek et al. |
| 5,290,245 | A | 3/1994 | Dennis |
| 5,290,249 | A | 3/1994 | Foster et al. |
| 5,308,336 | A | 5/1994 | Hart et al. |
| 5,312,391 | A | 5/1994 | Wilk |
| 5,312,417 | A | 5/1994 | Wilk |
| 5,314,417 | A | 5/1994 | Stephens et al. |
| 5,318,516 | A | 6/1994 | Cosmescu |
| 5,330,486 | A | 7/1994 | Wilk |
| 5,334,143 | A | 8/1994 | Carroll |
| 5,334,150 | A | 8/1994 | Kaali |
| 5,336,169 | A | 8/1994 | Divilio et al. |
| 5,336,203 | A | 8/1994 | Goldhardt et al. |
| 5,337,937 | A | 8/1994 | Remiszewski et al. |
| 5,345,927 | A | 9/1994 | Bonutti |
| 5,346,459 | A | 9/1994 | Mien |
| 5,360,417 | A | 11/1994 | Gravener et al. |
| 5,366,478 | A | 11/1994 | Brinkerhoff et al. |
| 5,375,588 | A | 12/1994 | Yoon |
| 5,378,588 | A | 1/1995 | Tsuchiya |
| 5,380,291 | A | 1/1995 | Kaali |
| 5,385,552 | A | 1/1995 | Haber et al. |
| 5,385,553 | A | 1/1995 | Hart et al. |
| 5,391,156 | A | 2/1995 | Hildwein et al. |
| 5,394,863 | A | 3/1995 | Sanford et al. |
| 5,395,367 | A | 3/1995 | Wilk |
| 5,407,433 | A | 4/1995 | Loomas |
| 5,431,151 | A | 7/1995 | Riek et al. |
| 5,437,683 | A | 8/1995 | Neumann et al. |
| 5,445,615 | A | 8/1995 | Yoon |
| 5,451,222 | A | 9/1995 | De Maagd et al. |
| 5,460,170 | A | 10/1995 | Hammerslag |
| 5,464,409 | A | 11/1995 | Mohajer |
| 5,480,410 | A | 1/1996 | Cuschieri et al. |
| 5,490,843 | A | 2/1996 | Hildwein et al. |
| 5,507,758 | A | 4/1996 | Thomason et al. |
| 5,511,564 | A | 4/1996 | Wilk |
| 5,514,133 | A | 5/1996 | Golub et al. |
| 5,514,153 | A | 5/1996 | Bonutti |
| 5,520,610 | A | 5/1996 | Giglio et al. |
| 5,520,698 | A | 5/1996 | Koh |
| 5,522,791 | A | 6/1996 | Leyva |
| 5,524,501 | A | 6/1996 | Patterson et al. |
| 5,524,644 | A | 6/1996 | Crook |
| 5,538,509 | A | 7/1996 | Dunlap et al. |
| 5,540,648 | A | 7/1996 | Yoon |
| 5,545,150 | A | 8/1996 | Danks et al. |
| 5,545,179 | A | 8/1996 | Williamson, IV |
| 5,549,565 | A | 8/1996 | Ryan et al. |
| 5,551,947 | A | 9/1996 | Kaali |
| 5,556,385 | A | 9/1996 | Andersen |
| 5,569,159 | A | 10/1996 | Anderson et al. |
| 5,569,205 | A | 10/1996 | Hart et al. |
| 5,569,291 | A | 10/1996 | Privitera et al. |
| 5,569,292 | A | 10/1996 | Scwemberger et al. |
| 5,577,993 | A | 11/1996 | Zhu et al. |
| 5,591,192 | A | 1/1997 | Privitera et al. |
| 5,601,581 | A | 2/1997 | Fogarty et al. |
| 5,609,562 | A | 3/1997 | Kaali |
| 5,624,399 | A | 4/1997 | Ackerman |
| 5,634,911 | A | 6/1997 | Hermann et al. |
| 5,634,937 | A | 6/1997 | Mollenauer et al. |
| 5,643,285 | A | 7/1997 | Rowden et al. |
| 5,649,550 | A | 7/1997 | Crook |
| 5,651,771 | A | 7/1997 | Fangherlini et al. |
| 5,653,705 | A | 8/1997 | de la Torre et al. |
| 5,656,013 | A | 8/1997 | Yoon |
| 5,672,168 | A | 9/1997 | de la Torre et al. |
| 5,683,378 | A | 11/1997 | Christy |
| 5,685,820 | A | 11/1997 | Riek et al. |
| 5,685,857 | A | 11/1997 | Negus et al. |
| 5,685,862 | A | 11/1997 | Mahurkar |
| 5,697,946 | A | 12/1997 | Hopper et al. |
| 5,709,671 | A | 1/1998 | Stephens et al. |
| 5,709,675 | A | 1/1998 | Williams |
| 5,713,858 | A | 2/1998 | Heruth et al. |
| 5,713,869 | A | 2/1998 | Morejon |
| 5,720,730 | A | 2/1998 | Blake, III |
| 5,720,761 | A | 2/1998 | Kaali |
| 5,722,962 | A | 3/1998 | Garcia |
| 5,728,103 | A | 3/1998 | Picha et al. |
| 5,730,748 | A | 3/1998 | Fogarty et al. |
| 5,735,791 | A | 4/1998 | Alexander, Jr. et al. |
| 5,741,298 | A | 4/1998 | MacLeod |
| 5,752,970 | A | 5/1998 | Yoon |
| 5,776,112 | A | 7/1998 | Stephens et al. |
| 5,782,817 | A | 7/1998 | Franzel et al. |
| 5,792,113 | A | 8/1998 | Kramer et al. |
| 5,795,290 | A | 8/1998 | Bridges |
| 5,800,451 | A | 9/1998 | Buess et al. |
| 5,803,921 | A | 9/1998 | Bonadio |
| 5,810,712 | A | 9/1998 | Dunn |
| 5,813,409 | A | 9/1998 | Leahy et al. |
| 5,830,191 | A | 11/1998 | Hildwein et al. |
| 5,836,871 | A | 11/1998 | Wallace et al. |
| 5,836,913 | A | 11/1998 | Orth et al. |
| 5,840,077 | A | 11/1998 | Rowden et al. |
| 5,842,971 | A | 12/1998 | Yoon |
| 5,848,992 | A | 12/1998 | Hart et al. |
| 5,853,417 | A | 12/1998 | Fogarty et al. |
| 5,857,461 | A | 1/1999 | Levitsky et al. |
| 5,865,817 | A | 2/1999 | Moenning et al. |
| 5,871,471 | A | 2/1999 | Ryan et al. |
| 5,871,474 | A | 2/1999 | Hermann et al. |
| 5,876,413 | A | 3/1999 | Fogarty et al. |
| 5,893,875 | A | 4/1999 | O'Connor et al. |
| 5,894,843 | A | 4/1999 | Benetti et al. |
| 5,895,377 | A | 4/1999 | Smith et al. |
| 5,899,208 | A | 5/1999 | Bonadio |
| 5,899,913 | A | 5/1999 | Fogarty et al. |
| 5,904,703 | A | 5/1999 | Gilson |
| 5,906,577 | A | 5/1999 | Beane et al. |
| 5,914,415 | A | 6/1999 | Tago |
| 5,916,198 | A | 6/1999 | Dillow |
| 5,941,898 | A | 8/1999 | Moenning et al. |
| 5,951,588 | A | 9/1999 | Moenning |
| 5,957,913 | A | 9/1999 | de la Torre et al. |
| 5,964,781 | A | 10/1999 | Mollenauer et al. |
| 5,976,174 | A | 11/1999 | Ruiz |
| 5,997,515 | A | 12/1999 | de la Torre et al. |
| 6,007,481 | A | 12/1999 | Riek et al. |
| 6,017,355 | A | 1/2000 | Hessel et al. |
| 6,018,094 | A | 1/2000 | Fox |
| 6,024,736 | A | 2/2000 | de la Torre et al. |
| 6,030,402 | A | 2/2000 | Thompson et al. |
| 6,033,426 | A | 3/2000 | Kaji |
| 6,033,428 | A | 3/2000 | Sardella |
| 6,042,573 | A | 3/2000 | Lucey |
| 6,048,309 | A | 4/2000 | Flom et al. |
| 6,059,816 | A | 5/2000 | Moenning |
| 6,068,639 | A | 5/2000 | Fogarty et al. |
| 6,077,288 | A | 6/2000 | Shimomura et al. |
| 6,086,603 | A | 7/2000 | Termin et al. |
| 6,093,176 | A | 7/2000 | Dennis |
| 6,099,505 | A | 8/2000 | Ryan et al. |

(56) References Cited

U.S. PATENT DOCUMENTS

| | | |
|---|---|---|
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,213,957 B1 | 4/2001 | Milliman et al. |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,355,028 B2 | 3/2002 | Castaneda et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,478,806 B2 | 11/2002 | McFarlane |
| 6,485,410 B1 | 11/2002 | Loy |
| 6,485,467 B1 | 11/2002 | Crook et al. |
| 6,487,806 B2 | 12/2002 | Murello et al. |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,551,282 B1 | 4/2003 | Exline et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,038 B2 | 9/2003 | Bonutti et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Fernstrom |
| 6,684,405 B2 | 2/2004 | Lezdey |
| 6,702,787 B2 | 3/2004 | Racenet et al. |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,736,797 B1 | 5/2004 | Larsen et al. |
| 6,740,064 B1 | 5/2004 | Sorrentino et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,835,201 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,855,128 B2 | 2/2005 | Swenson |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,942,671 B1 | 9/2005 | Smith |
| 6,945,932 B1 | 9/2005 | Caldwell et al. |
| 6,958,037 B2 | 10/2005 | Ewers et al. |
| 6,960,164 B2 | 11/2005 | O'Heeron |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,320,694 B2 | 1/2008 | O'Heeron |
| 7,331,940 B2 | 2/2008 | Sommerich |
| 7,344,547 B2 | 3/2008 | Piskun |
| 7,370,694 B2 | 5/2008 | Shimizu et al. |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,494,481 B2 | 2/2009 | Moberg et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,678,046 B2 | 3/2010 | White et al. |

(56) References Cited

U.S. PATENT DOCUMENTS

| | | |
|---|---|---|
| 7,686,823 B2 | 3/2010 | Pingleton et al. |
| 7,704,207 B2 | 4/2010 | Albrecht et al. |
| 7,708,713 B2 | 5/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,744,569 B2 | 6/2010 | Smith |
| 7,753,901 B2 | 7/2010 | Piskun et al. |
| 7,758,500 B2 | 7/2010 | Boyd et al. |
| 7,758,603 B2 | 7/2010 | Taylor et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,794,644 B2 | 9/2010 | Taylor et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,655 B2 | 12/2010 | Pasqualucci |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,918,827 B2 | 4/2011 | Smith |
| 7,947,058 B2 | 5/2011 | Kahle et al. |
| 7,951,076 B2 | 5/2011 | Hart et al. |
| 7,955,257 B2 | 6/2011 | Frasier et al. |
| 7,955,313 B2 | 6/2011 | Boismier |
| 7,985,232 B2 | 7/2011 | Potter et al. |
| 3,002,750 A1 | 8/2011 | Smith |
| 3,002,786 A1 | 8/2011 | Beckman et al. |
| 7,998,068 B2 | 8/2011 | Bonadio et al. |
| 3,012,128 A1 | 9/2011 | Franer et al. |
| 3,021,296 A1 | 9/2011 | Bonadio et al. |
| 3,025,670 A1 | 9/2011 | Sharp et al. |
| 8,029,475 B2 | 10/2011 | Franer et al. |
| 8,038,652 B2 | 10/2011 | Morrison et al. |
| 8,052,653 B2 | 11/2011 | Gratwohl et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,092,431 B2 | 1/2012 | Lunn et al. |
| 8,105,234 B2 | 1/2012 | Ewers et al. |
| 8,109,873 B2 | 2/2012 | Albrecht et al. |
| 8,118,735 B2 | 2/2012 | Voegele |
| 8,128,590 B2 | 3/2012 | Albrecht et al. |
| 8,137,318 B2 | 3/2012 | Schweitzer et al. |
| 8,147,453 B2 | 4/2012 | Albrecht et al. |
| 8,152,828 B2 | 4/2012 | Taylor et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,206,411 B2 | 6/2012 | Thompson et al. |
| 8,241,209 B2 | 8/2012 | Shelton, IV et al. |
| 8,262,568 B2 | 9/2012 | Albrecht et al. |
| 8,267,952 B2 | 9/2012 | Kahle et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,398,666 B2 | 3/2013 | McFarlane |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 8,597,180 B2 | 12/2013 | Copeland et al. |
| 8,961,406 B2 | 2/2015 | Ortiz et al. |
| 10,022,149 B2 | 7/2018 | Holsten et al. |
| 10,568,660 B2 | 2/2020 | Zhou |
| 10,653,449 B2 | 5/2020 | Main et al. |
| 2001/0037053 A1 | 11/2001 | Bonadio et al. |
| 2002/0055714 A1 | 5/2002 | Rothschild |
| 2002/0091410 A1 | 7/2002 | Ben-David et al. |
| 2002/0173748 A1 | 11/2002 | McConnell et al. |
| 2003/0014076 A1 | 1/2003 | Mollenauer et al. |
| 2003/0093104 A1 | 5/2003 | Bonner et al. |
| 2003/0109853 A1 | 6/2003 | Harding et al. |
| 2003/0187376 A1 | 10/2003 | Rambo |
| 2003/0187397 A1 | 10/2003 | Vitali |
| 2003/0233115 A1 | 12/2003 | Eversull et al. |
| 2003/0236549 A1 | 12/2003 | Bonadio et al. |
| 2004/0006356 A1 | 1/2004 | Smith |
| 2004/0054353 A1 | 3/2004 | Taylor |
| 2004/0059297 A1 | 3/2004 | Racenet et al. |
| 2004/0073090 A1 | 4/2004 | Butler et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0186434 A1 | 9/2004 | Harding et al. |
| 2004/0204682 A1 | 10/2004 | Smith |
| 2004/0204734 A1 | 10/2004 | Wagner et al. |
| 2004/0215209 A1 | 10/2004 | Almond et al. |
| 2004/0267096 A1 | 12/2004 | Caldwell et al. |
| 2004/0267204 A1 | 12/2004 | Brustowicz |
| 2005/0010238 A1 | 1/2005 | Potter et al. |
| 2005/0020884 A1 | 1/2005 | Hart et al. |
| 2005/0033342 A1 | 2/2005 | Hart et al. |
| 2005/0070850 A1 | 3/2005 | Albrecht |
| 2005/0070851 A1 | 3/2005 | Thompson et al. |
| 2005/0070935 A1 | 3/2005 | Ortiz |
| 2005/0070946 A1 | 3/2005 | Franer et al. |
| 2005/0070947 A1 | 3/2005 | Franer et al. |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0192594 A1 | 9/2005 | Skakoon et al. |
| 2005/0203346 A1 | 9/2005 | Bonadio et al. |
| 2005/0209608 A1 | 9/2005 | O'Heeron |
| 2005/0212221 A1 | 9/2005 | Smith et al. |
| 2005/0222582 A1 | 10/2005 | Wenchell |
| 2005/0245876 A1 | 11/2005 | Khosravi et al. |
| 2005/0251092 A1 | 11/2005 | Howell et al. |
| 2005/0251190 A1 | 11/2005 | McFarlane |
| 2005/0277946 A1 | 12/2005 | Greenhalgh |
| 2006/0020281 A1 | 1/2006 | Smith |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0211992 A1 | 9/2006 | Prosek |
| 2006/0212063 A1 | 9/2006 | Wilk |
| 2006/0217665 A1 | 9/2006 | Prosek |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2006/0276751 A1 | 12/2006 | Haberland et al. |
| 2007/0088277 A1 | 4/2007 | McGinley et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |

(56) References Cited

U.S. PATENT DOCUMENTS

| | | |
|---|---|---|
| 2007/0239108 A1 | 10/2007 | Albrecht et al. |
| 2007/0255218 A1* | 11/2007 | Franer ............... A61B 17/3462 604/167.02 |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0051739 A1 | 2/2008 | McFarlane |
| 2008/0058723 A1 | 3/2008 | Lipchitz et al. |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0146884 A1 | 6/2008 | Beckman et al. |
| 2008/0161758 A1 | 7/2008 | Insignares |
| 2008/0161826 A1 | 7/2008 | Guiraudon |
| 2008/0177265 A1 | 7/2008 | Lechot |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0208222 A1 | 8/2008 | Beckman et al. |
| 2008/0249475 A1 | 10/2008 | Albrecht et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093835 A1 | 4/2009 | Heinrich et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0234293 A1 | 9/2009 | Albrecht et al. |
| 2009/0275880 A1 | 11/2009 | Pasqualucci |
| 2009/0326330 A1 | 12/2009 | Bonadio et al. |
| 2009/0326332 A1 | 12/2009 | Carter |
| 2010/0016800 A1 | 1/2010 | Rockrohr |
| 2010/0030155 A1 | 2/2010 | Gyrn et al. |
| 2010/0049138 A1 | 2/2010 | Smith et al. |
| 2010/0063450 A1 | 3/2010 | Smith et al. |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0222801 A1 | 9/2010 | Pingleton et al. |
| 2010/0228090 A1 | 9/2010 | Weisenburgh, II |
| 2010/0228094 A1 | 9/2010 | Ortiz et al. |
| 2010/0228096 A1 | 9/2010 | Weisenburgh, II et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0261975 A1 | 10/2010 | Huey et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0286706 A1 | 11/2010 | Judson |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118553 A1 | 5/2011 | Stopek |
| 2011/0118833 A1 | 5/2011 | Reichenbach et al. |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0190592 A1 | 8/2011 | Kahle et al. |
| 2011/0201891 A1 | 8/2011 | Smith et al. |
| 2011/0237901 A1* | 9/2011 | Duke ............... A61B 17/3462 600/208 |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251559 A1 | 10/2011 | Tal et al. |
| 2011/0251560 A1 | 10/2011 | Albrecht et al. |
| 2011/0251633 A1 | 10/2011 | Smith |
| 2011/0276002 A1 | 11/2011 | Bierman |
| 2011/0313250 A1 | 12/2011 | Kleyman |
| 2012/0010569 A1 | 1/2012 | Parihar |
| 2012/0041371 A1 | 2/2012 | Tal et al. |
| 2012/0059640 A1 | 3/2012 | Roy et al. |
| 2012/0065590 A1 | 3/2012 | Bierman et al. |
| 2012/0109064 A1 | 5/2012 | Fischvogt et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2012/0316596 A1 | 12/2012 | Taylor et al. |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0025477 A1 | 1/2015 | Evans |
| 2015/0065808 A1 | 3/2015 | Van Wyk et al. |
| 2015/0223833 A1 | 8/2015 | Coffeen et al. |
| 2018/0021063 A1* | 1/2018 | Main ............... A61B 17/3474 604/167.01 |
| 2018/0085145 A1* | 3/2018 | Okoniewski ....... A61B 17/3462 |
| 2019/0059938 A1 | 2/2019 | Holsten |

(56) References Cited

U.S. PATENT DOCUMENTS

2019/0059944 A1    2/2019  Holsten
2020/0246043 A1    8/2020  Holsten et al.

OTHER PUBLICATIONS

Extended European Search Report dated Nov. 25, 2021 issued in corresponding EP Appln. No. 21163414.2.

* cited by examiner

INSTRUMENT SEAL FOR SURGICAL ACCESS ASSEMBLY

FIELD

The present disclosure relates generally to access assemblies including seals for minimally invasive surgery. More particularly, the present disclosure relates to instrument seals for surgical access assemblies.

BACKGROUND

In order to facilitate minimally invasive surgery, a working space must be created at a surgical site. An insufflation fluid, typically $CO_2$, is introduced into the abdomen of the patient to create an inflated state called pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals that adapt to the surgical instrumentation. Typically, a "zero-seal" in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust seal capable adjusting to multiple sizes and withstanding multiple insertions and withdrawals of surgical instrumentation. Some of the surgical instrumentation can include sharp edges that can tear or otherwise damage seals. Therefore, it would be beneficial to have an access assembly with improved seal durability.

SUMMARY

In an embodiment, a surgical access assembly includes a housing, a tubular member extending from the housing, and a valve assembly disposed in the housing. The valve assembly includes a centering mechanism, a guard assembly, and an instrument seal. The centering mechanism has a central opening. The guard assembly has a central orifice that is alignable with the central opening of the centering mechanism. The guard assembly is disposed on a first side of the centering mechanism. The instrument seal includes a central hole alignable with the central opening of the centering mechanism and is disposed on a second side of the centering mechanism opposite the first side of the centering mechanism and proximate the tubular member. The instrument seal includes petals that are arranged such that a portion of one petal covers a portion of a first adjacent petal and is covered by a portion of a second adjacent petal.

The surgical access assembly may also include a retainer having first and second rings. The first ring may be disposed on the first side of the centering mechanism and the second side may be disposed on the second side of the centering mechanism. The retainer may sandwich the centering mechanism between the guard assembly and the instrument seal. The first ring may include pins extending therefrom and the second ring may include openings for receiving the pins therein.

The central opening of the centering mechanism may be circumscribed by a lip with pores extending therethrough, the guard assembly may include a ring with bores extending therethrough, and the instrument seal may include holes extending therethrough. The pins of the first ring may extend through the bores of the guard assembly, the pores of the centering mechanism, and the holes of the instrument seal to maintain the guard assembly, the centering mechanism, and the instrument seal in an aligned relationship. The pins of the first ring may be received in the openings of the second ring.

The instrument seal may have a frame that defines the central hole. The petals may be flexibly coupled to the frame. The petals may be coupled to the frame with living hinges.

In embodiments, a surgical access assembly has a housing, a tubular member extending from the housing, and a valve assembly disposed in the housing. The valve assembly includes a guard assembly with a central orifice and an instrument seal having a central hole aligned with the central orifice of the guard assembly. The instrument seal includes a frame with petals that are flexibly coupled to the frame. The instrument seal has an unfolded configuration defined by the petals extending away from a center of the frame and a folded configuration defined by the petals folded towards the central hole of the instrument seal such that each petal at least partially overlaps an adjacent petal such that the petals interlock.

The folded configuration of the instrument seal may define a diameter of the central hole that is configured to seal against a surgical instrument.

The petals may be flexibly coupled to the frame with living hinges.

The folded configuration of the instrument seal may allow the petals to flex relative to the frame while the frame may remain axially stationary relative to the housing.

The valve assembly may include a centering mechanism with a central opening. The guard assembly may be disposed on a first side of the centering mechanism and the instrument seal may be disposed on a second side of the centering mechanism that is opposite the first side.

The valve assembly may also include a retainer with first and second rings. The first ring may be disposed on the first side of the centering mechanism and the second ring may be disposed on the second side of the centering mechanism. The retainer may sandwich the centering mechanism between the guard assembly and the instrument seal.

The first ring of the retainer may include pins and the second ring of the retainer may include openings for receiving the pins. The pins of the first ring may be insertable through bores of the guard assembly, pores of the centering mechanism, and holes of the instrument seal to maintain the guard assembly, the centering mechanism, and the instrument seal in an aligned relationship.

In another embodiment, a surgical access assembly has a housing, a tubular member extending from the housing, and a valve assembly disposed in the housing. The valve assembly includes a centering mechanism with a central opening and an instrument seal in an abutting relationship with the centering mechanism. The instrument seal has a frame and petals. A first end of each petal is flexibly coupled to an outer surface of the frame and a second end of each petal is repositionable between a first position where the second end is outside a perimeter of the frame and a second position where the second end is inside the perimeter of the frame. Each petal partially overlaps an adjacent petal such that the petals interlock.

The instrument seal may have a central hole defined by the second position of the petals. The central hole may define a diameter configured to seal against a surgical instrument. The central hole of the instrument seal may be alignable with the central opening of the centering mechanism.

The valve assembly may also include first and second rings. The first ring may be disposed adjacent the centering mechanism and the second ring may be disposed adjacent the instrument seal. The centering mechanism and the instrument seal may be sandwiched between the first and second rings.

The first ring may have pins extending therefrom and the second ring may have openings for receiving the pins therein.

The valve assembly may also include a guard assembly with a central orifice. The guard assembly may be disposed between the first ring and the centering mechanism.

In a further embodiment, a surgical access assembly includes a housing, a tubular member extending from the housing, and an instrument seal disposed in the housing. The instrument seal has a frame with a plurality of frame arms. Each frame arm of the plurality of frame arms is flexibly coupled to at least one other frame arm of the plurality of frame arms. The instrument seal also includes a plurality of petals corresponding to the plurality of frame arms. The plurality of petals is arranged such that a portion of a first petal of the plurality of petals covers a portion of a first adjacent petal of the plurality of petals and is covered by a portion of a second adjacent petal of the plurality of petals. Each petal of the plurality of petals is flexibly coupled to the corresponding frame arm of the plurality of frame arms. The instrument seal further includes a plurality of fins flexibly coupled to the plurality of frame arms. Each fin of the plurality of fins is biased away from the corresponding frame arm of the plurality of frame arms. The plurality of fins is configured to engage an inner surface of the housing.

The plurality of fins may be configured to urge the instrument seal towards a center of the housing.

Movement of the instrument seal relative to a central longitudinal axis of the housing may compress one or more of the fins of the plurality of fins.

The instrument seal may further include a central hole aligned with a central longitudinal axis of the housing. The central hole may be configured to seal against a surgical instrument.

The surgical access assembly may further include a guard assembly with a central orifice. The guard assembly may be disposed on a first side of the instrument seal.

The surgical access assembly may further include a retainer. The retainer may have first and second discs sandwiching the guard assembly and the instrument seal therebetween.

The instrument seal may include orifices extending through each petal of the plurality of petals and the guard assembly may include bores extending therethrough.

The first disc may include pins and the second disc may include openings for receiving the pins. The pins may be insertable through the bores and the orifices to maintain the guard assembly and the instrument seal in an aligned relationship.

Each petal of the plurality of petals may be adapted to flex relative to the frame while the frame remains axially stationary relative to the housing.

BRIEF DESCRIPTION OF DRAWINGS

Embodiments of an instrument seal are disclosed herein with reference to the drawings, wherein.

DETAILED DESCRIPTION

Figure 1:
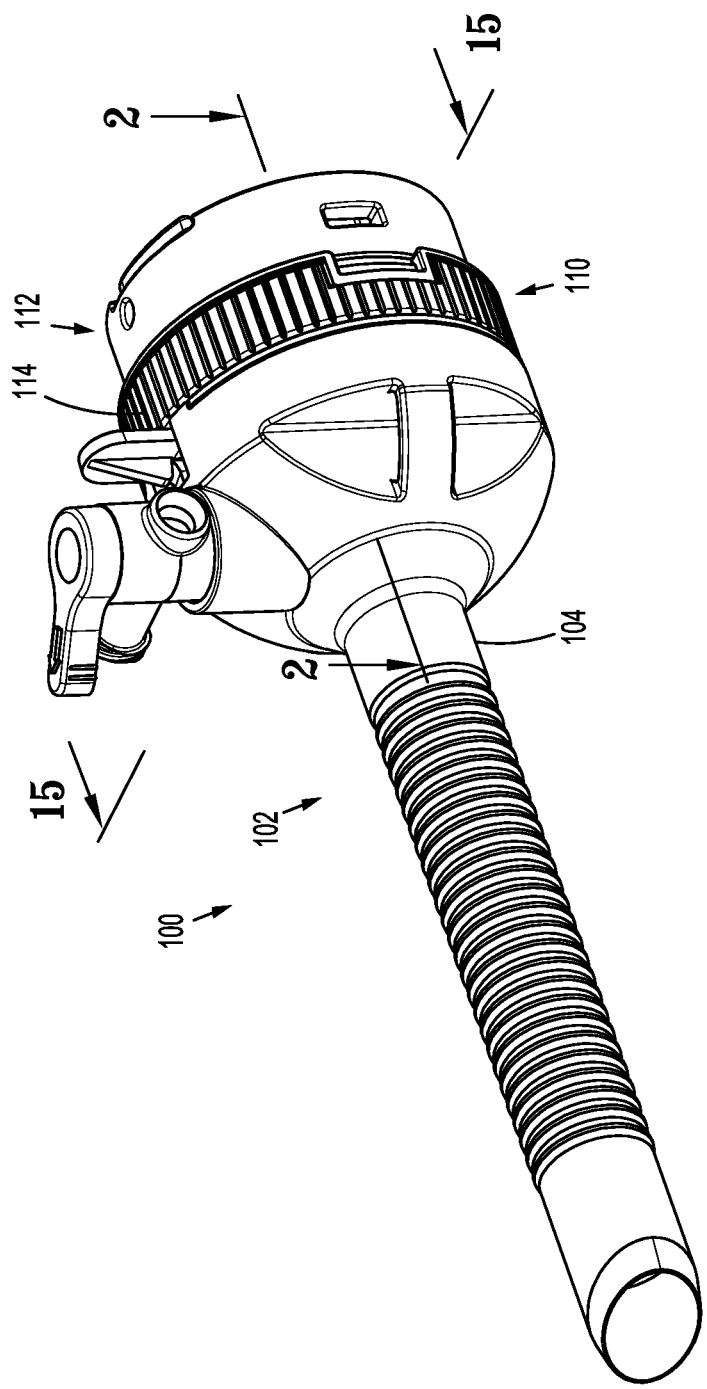
FIG. 1 is a perspective view of a surgical access assembly according to an embodiment of the present disclosure.

Embodiments of the presently disclosed instrument seal for a surgical access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Surgical access assemblies are employed during minimally invasive surgery, e.g., laparoscopic surgery, and provide for the sealed access of surgical instruments into an insufflated body cavity, such as the abdominal cavity. The surgical access assemblies of the present disclosure include an instrument valve housing mounted on a cannula tube, and include an obturator (not shown) inserted through the instrument valve housing and cannula tube. The obturator can have a blunt distal end, or a bladed or non-bladed penetrating distal end and can be used to incise the abdominal wall so that the surgical access assembly can be introduced into the abdomen. The handle of the obturator can engage or selectively lock into the instrument valve housing of the surgical access assembly.

Surgical access assemblies with a trocar obturator are employed to tunnel through an anatomical structure, e.g., the abdominal wall, either by making a new passage through the structure or by passing through an existing opening through the anatomical structure. Once the surgical access assembly with the trocar has tunneled through the anatomical structure, the trocar obturator is removed, leaving the surgical access assembly in place. The instrument valve housing of the surgical access assembly includes valves that prevent the escape of insufflation fluid from the body cavity, while also allowing surgical instruments to be inserted into the cavity and minimizing the escape of insufflation fluid.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of the obturator. The bladeless obturator may be provided for the blunt dissection of the abdominal lining during a surgical procedure.

Various trocar obturators suitable for use with the surgical access assemblies of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905 ("the '905 publication"), the content of which is hereby incorporated by reference herein in its entirety.

With initial reference now to FIG. 1, a surgical access assembly according to aspects of the present disclosure is shown generally as cannula assembly 100. The cannula assembly 100 includes a cannula 102 and an instrument valve housing 110 secured to the cannula 102. For a detailed description of an exemplary cannula assembly, please refer to the '905 publication.

Figure 2:
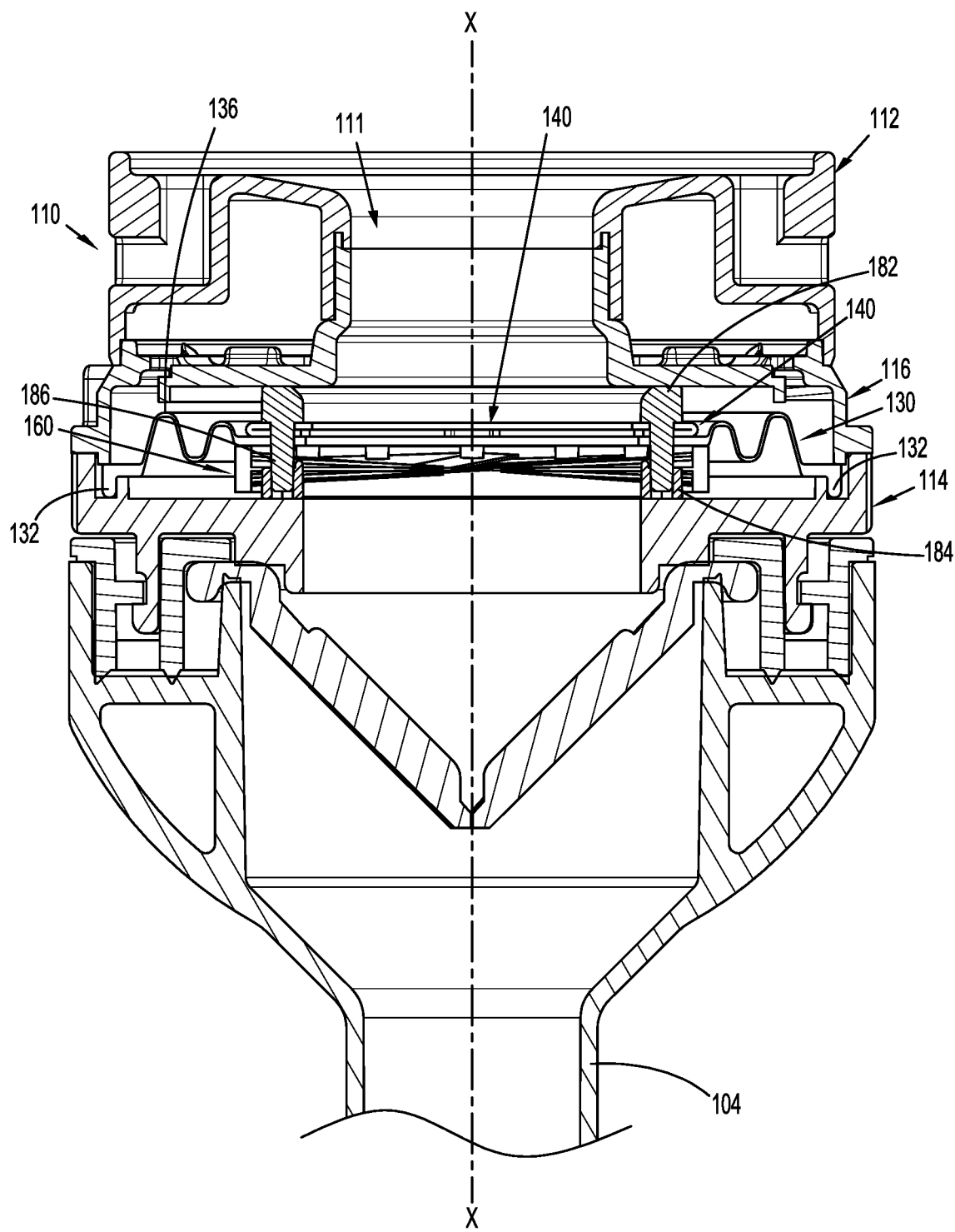
FIG. 2 is a cross-sectional view of the surgical access assembly of FIG. 1 taken along section line 2-2 of FIG. 1.

With additional reference to FIG. 2, the instrument valve housing 110 of the cannula assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the instrument valve housing 110 may be selectively attachable to, and detachable from, the inner housing section 116. The lower housing section 114 may be releasably or permanently attached to a cannula tube 104 of the cannula assembly 102. In embodiments, either or both of the upper and lower housing sections 112, 114 of the instrument valve housing 110 may include knurls, indentations, tabs, or be otherwise configured to facilitate engagement by a clinician.

The cannula assembly 100 may also include features for the stabilization of the surgical access assembly. For example, the distal end of the cannula tube 104 can carry a balloon anchor or another expandable member that engages the abdomen from the interior side. For example, see U.S. Pat. No. 7,300,448, the entire disclosure of which is hereby incorporated by reference herein. A feature on the opposite side of the abdominal wall can be used to further stabilize the surgical access assembly, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument through the cannula assembly 100.

Figure 3:
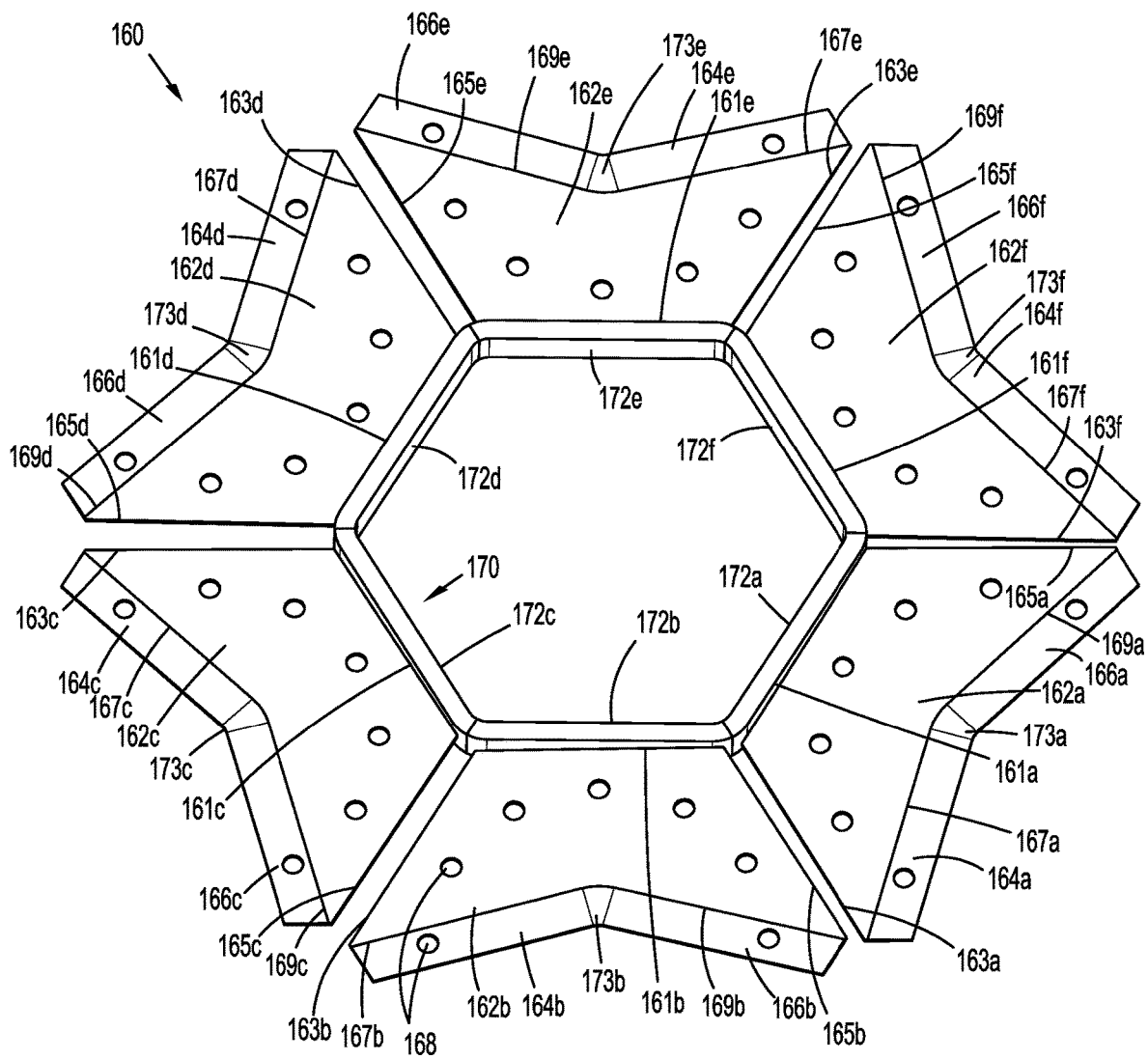
FIG. 3 is a top perspective view of an instrument seal in an unfolded configuration according to an embodiment of the present disclosure.
Figure 4:
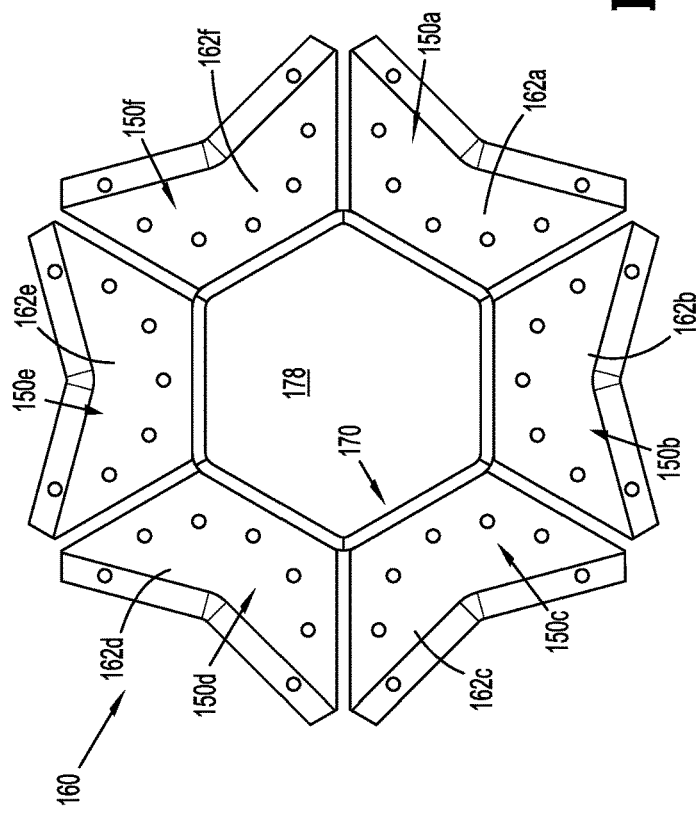
FIG. 4 is a top plan view of the instrument seal of FIG. 3.
Figure 5:
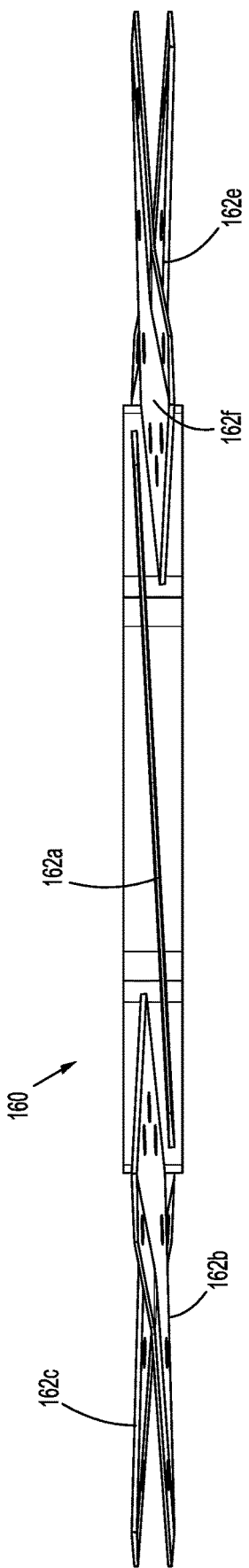
FIG. 5 is a side elevational view of the instrument seal of FIG. 4.

Referring now to FIGS. 3-5, an instrument seal 160, according to an embodiment of the present disclosure, is illustrated. The instrument seal 160, as illustrated, includes a hexagonal frame 170 that may be integrally formed (i.e., monolithic or unitary) or may be formed from six discrete segments that are joined together to form the frame 170. The segments may be joined to each other by welding, adhesives, mechanical joints, or other techniques as known in the art. The sides or segments 172a-f of the frame 170 form a boundary that defines a passage 178 having a center through the instrument seal 160. The center of the passage 178 is coaxial with a central hole 176 of the instrument seal 160. A corresponding number of petals 162 are attached to the frame 170. Although depicted with six petals 162a-f coupled to a hexagonal frame 170, the instrument seal may include a frame with more sides or discrete segments and a corresponding number of petals (e.g., 8). Alternatively, the presently disclosed instrument seal may include a frame with fewer sides or discrete segments and a corresponding number of petals (e.g., 4). The frame 170 and the petals 162a-f may be fabricated from a polyisoprene, a liquid silicone rubber, or another suitable polymeric material. The instrument seal 160 may be molded, stamped, or formed in any other suitable manner. Each petal 162a-f is flexibly coupled to a side 172a-f of the frame 170 via a living hinge 174a-f. Further, as shown in FIGS. 3 and 5, each petal 162a-f is attached to the corresponding side 172a-f of the frame 170 via the living hinge 174a-f such that each petal 162a-f and the corresponding living hinge 174a-f define an acute angle with respect to either a top or bottom surface of the side or segment of the frame 170. The acute angle may be in the range of about 3° to about 10°. By angling each petal 162a-f relative to the top or bottom surface of the frame 170, interweaving the petals 162a-f of the instrument seal 160 is easier than if each petal 162a-f was parallel with the top or bottom surface of the frame 170.

Figure 7:
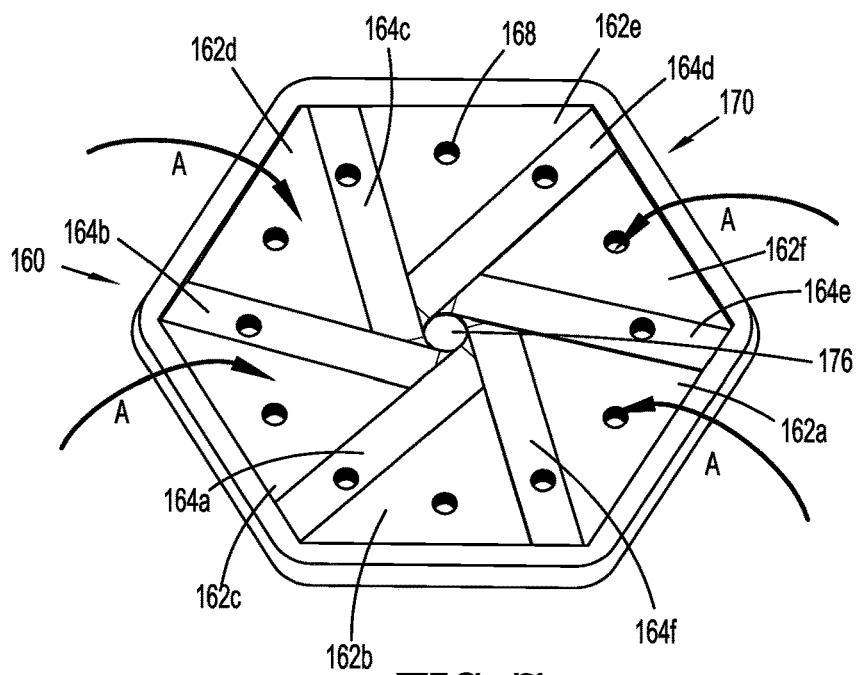
FIG. 7 is a top perspective view of the instrument seal of FIG. 4 in a fully folded configuration illustrating the folding sequence of the petals.

Each petal 162a-f is a five sided main panel 150a-f with holes 168 extending therethrough. Although shown with five sides, each main panel 150a-f may have more or less than five sides. A first or connection side 161a-f is coupled to a side or segment 172a-f of the frame 170 with the corresponding living hinge 174a-f. This arrangement allows the petal 162a-f to be transitioned from an unfolded configuration (FIG. 3) to a folded configuration (FIG. 7). Each living hinge 174a-f may be formed from the same material as the frame 170 and the petals 162a-f or may be formed from another suitable polymeric material. In the unfolded configuration, each petal 162a-f extends away from an outer surface of the frame 170 outside a perimeter defined by the frame 170. In the folded configuration, each petal 162a-f is bounded by the frame 170 and is within the perimeter defined by the frame 170. Each main panel 150a-f has angled second and third sides 163a-f, 165a-f that extend from the connection side 161a-f in a divergent manner. Fourth and fifth sides 167a-f, 169a-f of main panels 150a-f interconnect the angled second and third sides 163a-f, 165a-f. The fourth and fifth sides 167a-f, 169a-f of the main panels 150a-f of each petal 162a-f have equal lengths and are angled towards the corresponding connection side 161a-f such that they meet a point that would bisect the connection side 161a-f. Additionally, the fourth and fifth sides 167a-f, 169a-f are oriented such that they define an angle between 120° and 160°. First and second extenders 164a-f, 166a-f are attached to the fourth and fifth sides 167a-f, 169a-f. Each extender 164a-f, 166a-f includes a hole 168 extending therethrough. The first and second extenders 164a-f, 166a-f have equal lengths and meet at wedges 173a-f that also is located at a point that would bisect the connection side 161a-f. The extenders 164a-f, 166a-f and the main panels 150*a-f* of each petal 162*a-f* bend at a midpoint between the second and third sides 163*a-f*, 165*a-f* of each petal 162*a-f* such that, when viewed from the end (i.e., from the extenders towards the connection side) (see FIG. 5), the petal 162*a-f* has a slight curvature of about 3° to about 10°. The combination of the petals' 162*a-f* curvature, the angled relationship between each petal 162*a-f* and the side or segment 172*a-f* of the frame 170, and the material of construction, facilitates folding the petals 162*a-f* in an interlocking pattern when transitioning the instrument seal 160 from the unfolded configuration to the folded configuration.

Figure 6:
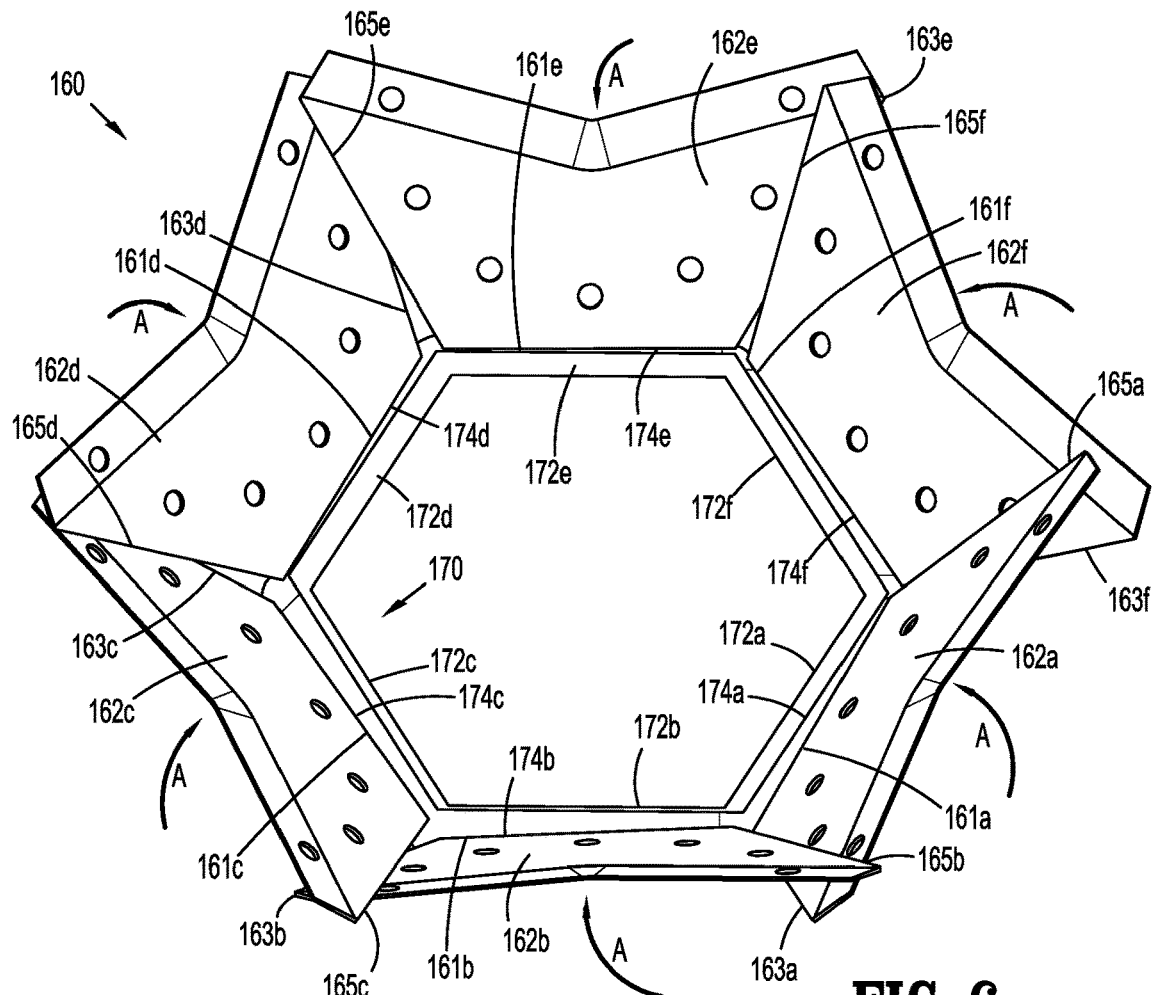
FIG. 6 is a top perspective view of the instrument seal of FIG. 4 in a partially folded configuration.

With reference now to FIGS. 3, 6, and 7, transitioning the instrument seal 160 from the unfolded configuration (FIG. 3) to the folded configuration (FIG. 7) includes folding the petals 162*a-f* sequentially such that they interlock by having each petal 162*a-f* partially overlap an adjacent petal 162*a-f*. Initially, as seen in FIG. 3, the instrument seal 160 is in the unfolded configuration with the extenders 164*a-f*, 166*a-f* of the petals 162*a-f* facing away from the frame 170. Each petal 162*a-f* is folded along a line defined by the associated living hinge 174*a-f* which defines an angle between the connection side 161*a-f* of the respective petal 162*a-f* and the corresponding side or segment 172*a-f* of the frame 170. Thus, the intersection of the connection side 161*a-f* and the corresponding third side 165*a-f* of each petal 162*a-f* is closer to the side or segment 172*a-f* of the frame 170 than the intersection of the connection side 161*a-f* and the second side 163*a-f* of each petal 162*a-f* is to the side or segment 172*a-f* of the frame 170. The petals 162*a-f* are folded sequentially in the direction of arrows "A" such that all of the petals 162*a-f* are in a near vertical orientation (FIG. 6). In this arrangement, the second side 163*a-f* of one petal 162*a-f* partially overlaps the third side 165*a-f* of the adjacent petal 162*a-f*. In particular, as illustrated in FIG. 6, the third side 165*a* of the first petal 162*a* partially overlaps the second side 163*f* of the sixth petal 162*f*, the third side 165*b* of the second petal 162*b* partially overlaps the second side 163*a* of the first petal 162*a*, the third side 165 of the third petal 162*c* partially overlaps the second side of the second petal 162*b*, the third side 165*d* of the fourth petal 162*d* partially overlaps the second side 163*c* of the third petal 162*c*, the third side 165*e* of the fifth petal 162*e* partially overlaps the second side 163*d* of the fourth petal 162*d*, the third side 165*f* of the sixth petal 162*f* partially overlaps the second side 163*e* of the fifth petal 162*e*, and the third side 165*a* of the first petal 162*a* partially overlaps the second side 163*f* of the sixth petal 162*f*. This defines a partially folded configuration of the instrument seal 160. Subsequently, the user continues to fold the petals 162*a-f* towards a center of the frame 170 in the direction of arrows "A" while maintaining the overlapping arrangement between the second and third sides 163*a-f*, 165*a-f* of the petals 162*a-f*. Once all the petals 162*a-f* are folded such that they are substantially flush with a top surface of the frame 170, the overlapping arrangement of the second and third sides 163*a-f*, 165*a-f* of the petals 162*a-f* maintains the petals 162*a-f* in contact with one another thereby maintaining the instrument seal 160 in the folded configuration. Further, once all the petals 162*a-f* are folded over, the holes 168 of the petals 162*a-f* are aligned thereby allowing pins 186 of a retainer 180 to pass therethrough as will be discussed in detail hereinbelow. As seen in FIG. 7, the folded configuration of the instrument seal 160 defines a central hole 176 for slidably receiving a surgical instrument therethrough. The central hole 176 may have a diameter between 0.025 inches to 0.100 inches (i.e., 0.0635 cm to 0.254 cm).

Figures 8, 9:
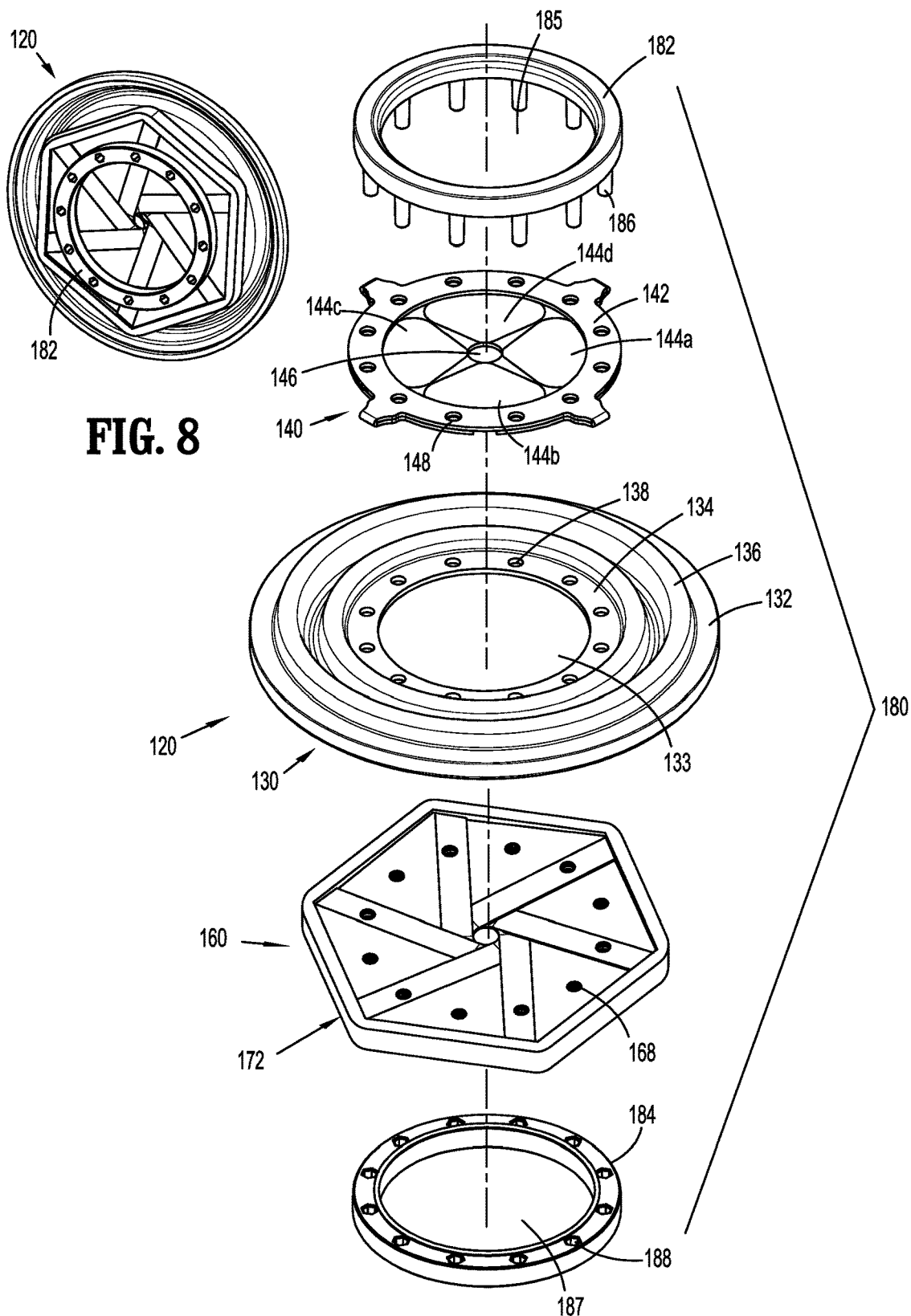
FIG. 8 is a bottom perspective view of a valve assembly according to an embodiment of the present disclosure.
FIG. 9 is an exploded view, with parts separated, of the valve assembly of FIG. 8 including a centering mechanism, a guard assembly, a retainer, and the instrument seal of FIG. 3.

With reference now to FIGS. 2, 8, and 9, the valve assembly 120, according to an embodiment of the present disclosure, is illustrated. The valve assembly 120 is located in the instrument valve housing 110 and includes a centering mechanism 130, a guard assembly 140, the instrument seal 160, and a retainer 180. The centering mechanism 130 of the valve assembly 120 permits radial movement of the valve assembly 120 relative to a central longitudinal axis "X" of the instrument valve housing 110 in response to insertion of a surgical instrument (not shown) through the valve assembly 120 and radial movement of the surgical instrument relative to the central longitudinal axis "X". In the absence of a surgical instrument or in the absence of radial movement of a surgical instrument relative to the central longitudinal axis "X", the centering mechanism 130, as will be described in detail hereinbelow, returns the valve assembly 120 to a generally centered position such that a central opening 133 of the centering mechanism 130 and the central longitudinal axis "X" are coaxial. The guard assembly 140 protects the instrument seal 160 during insertion and withdrawal of a surgical instrument through the instrument seal 160, which, as discussed hereinabove, provides for sealed passage of the surgical instrument through the instrument valve housing 110. The retainer 180 includes first and second rings 182, 184 that are located on opposing sides of the centering mechanism 130 for maintaining relative positions of the guard assembly 140, the centering mechanism 130, and the instrument seal 160. Additionally, the retainer maintains 180 an aligned relationship of the guard assembly 140, the centering mechanism 130, and the instrument seal 160. In particular, the first ring 182 of the retainer 180 includes pins 186 that extend from a bottom surface of the first ring 182 while the second ring 184 of the retainer 180 includes complementary openings 188 for receiving the pins 186 of the first ring 182. The pins 186 may be releasably engaged with the openings 188 or the pins 186 may be secured within the openings 188 by welding, adhesives, friction fit, or other techniques as are known in the art. The pins 186 are insertable through bores 148 of the guard assembly 140, pores 138 of the centering mechanism 130, the holes 168 of the instrument seal 160, and the openings 188 of the second ring 184 of the retainer 180. This arrangement aligns the relative positions of the guard assembly 140, the centering mechanism 130, and the instrument seal 160. Although illustrated with pins 186 extending from the first ring 182 towards openings 188 in the second ring 184, the retainer may have the pins located on the second ring and the openings on the first ring. Alternatively, the first and second rings may have an alternating arrangement of pins and openings that are complementary such that the pins of one of the rings align with openings of the other of the rings allowing the rings to be attached to one another and define the retainer. The first ring 182 defines a central opening 185 extending therethrough and the second ring 184 defines a central opening 187 extending therethrough.

The centering mechanism 130 of the instrument valve housing 110 is configured to maintain the valve assembly 120 centered within the instrument valve housing 110. More particularly, the centering mechanism 130 includes an outer annular ring 132, an inner annular ring 134, and a bellows 136 disposed between the outer annular ring 132 and the inner annular ring 134. As shown in FIG. 2, the outer annular ring 132 is received between the inner housing section 116 and the lower housing section 114 to retain the centering mechanism 130 within the instrument valve housing 110. The inner annular ring 134 supports the guard assembly 140. For a detailed description of the structure and function of an exemplary centering mechanism, please refer to U.S. Pat. No. 6,702,787, the content of which is incorporated herein by reference in its entirety.

The guard assembly 140 may be formed from a sheet of a plastic or other suitable polymeric material by stamping with a tool that forms a ring 142 and blades 144a-d. The ring 142 surrounds the blades 144a-d and includes bores 148 extending therethrough for slidably receiving the pins 186 of the first ring 182 of the retainer 180. Further, when the valve assembly 120 is assembled, the guard assembly 140 is positioned between one side of the centering mechanism 130 and the first ring 182 of the retainer 180. The blades 144a-d are configured to flex towards the centering mechanism 130 in response to insertion of a surgical instrument (not shown) through a central orifice 146 of the guard assembly 140 and return to a generally planar configuration (i.e., parallel with the ring) once the surgical instrument is removed. The blades 144a-d extend towards a center of the ring 142 and define the central orifice 146 which has a diameter greater than an outside diameter of the surgical instrument.

During a surgical procedure utilizing cannula assembly 100, a surgical instrument (not shown) is introduced into the instrument valve housing 110 through the longitudinal passage 111 in the upper, lower, and inner housing sections 112, 114, 116. As described above, the distal end of the surgical instrument engages one or more of the blades 144a-d of the guard assembly 140 causing the blades 144a-d to flex downward into contact with the petals 162a-f of the instrument seal 160. This causes the central hole 176 of the instrument seal 160 to dilate such that the diameter of the central hole 176 is sufficiently large enough to accommodate passage of the surgical instrument therethrough. The guard assembly 140 minimizes damage to the instrument seal 160 during insertion and/or removal of the surgical instrument through the valve assembly 120. The guard assembly 140 operates to protect the instrument seal 160 and minimizes tearing or other damage as the surgical instrument is received through and withdrawn from the instrument seal 160.

Figure 10:
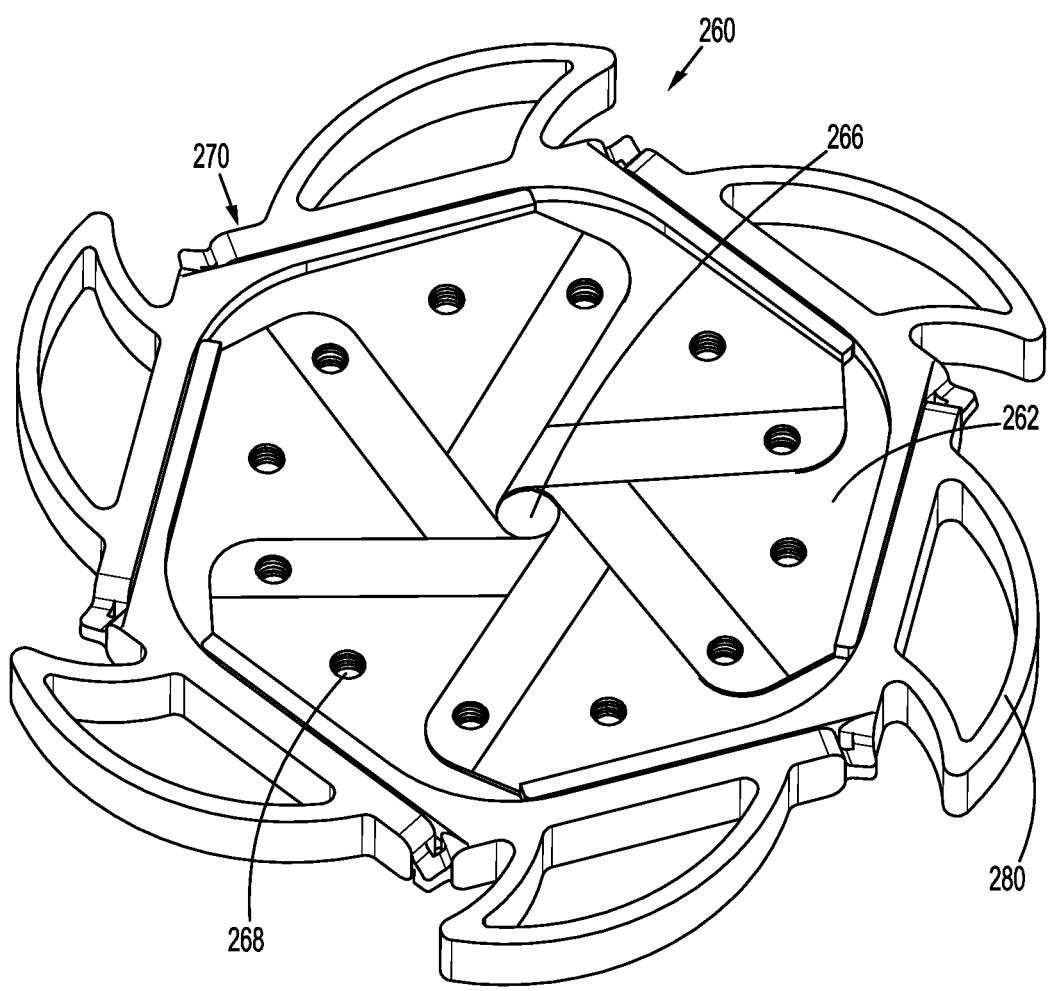
FIG. 10. is a top perspective view of an instrument seal according to an alternate embodiment of the present disclosure.
Figure 11:
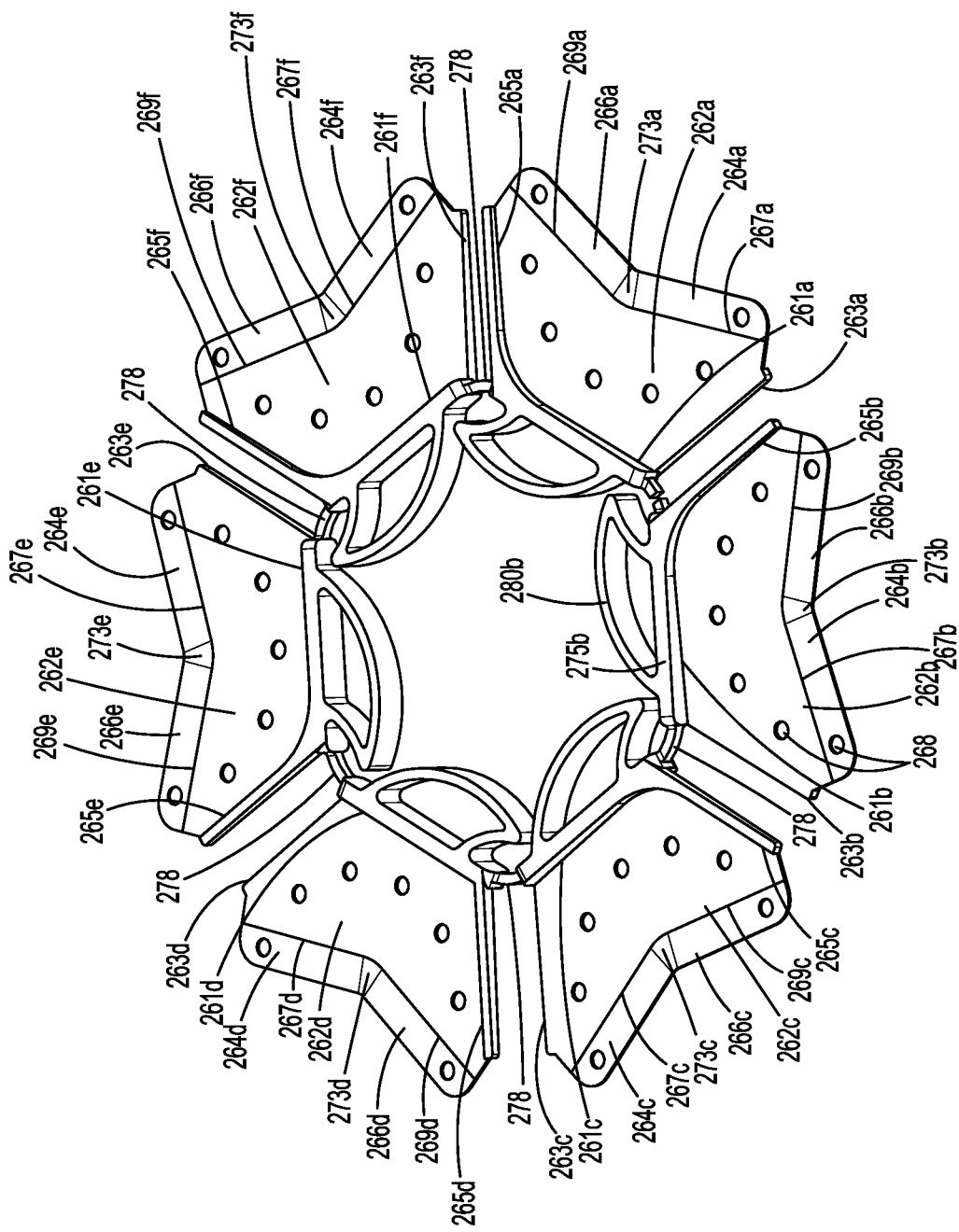
FIG. 11 is a top perspective view of the instrument seal of FIG. 10 in an unfolded configuration.
Figure 12:
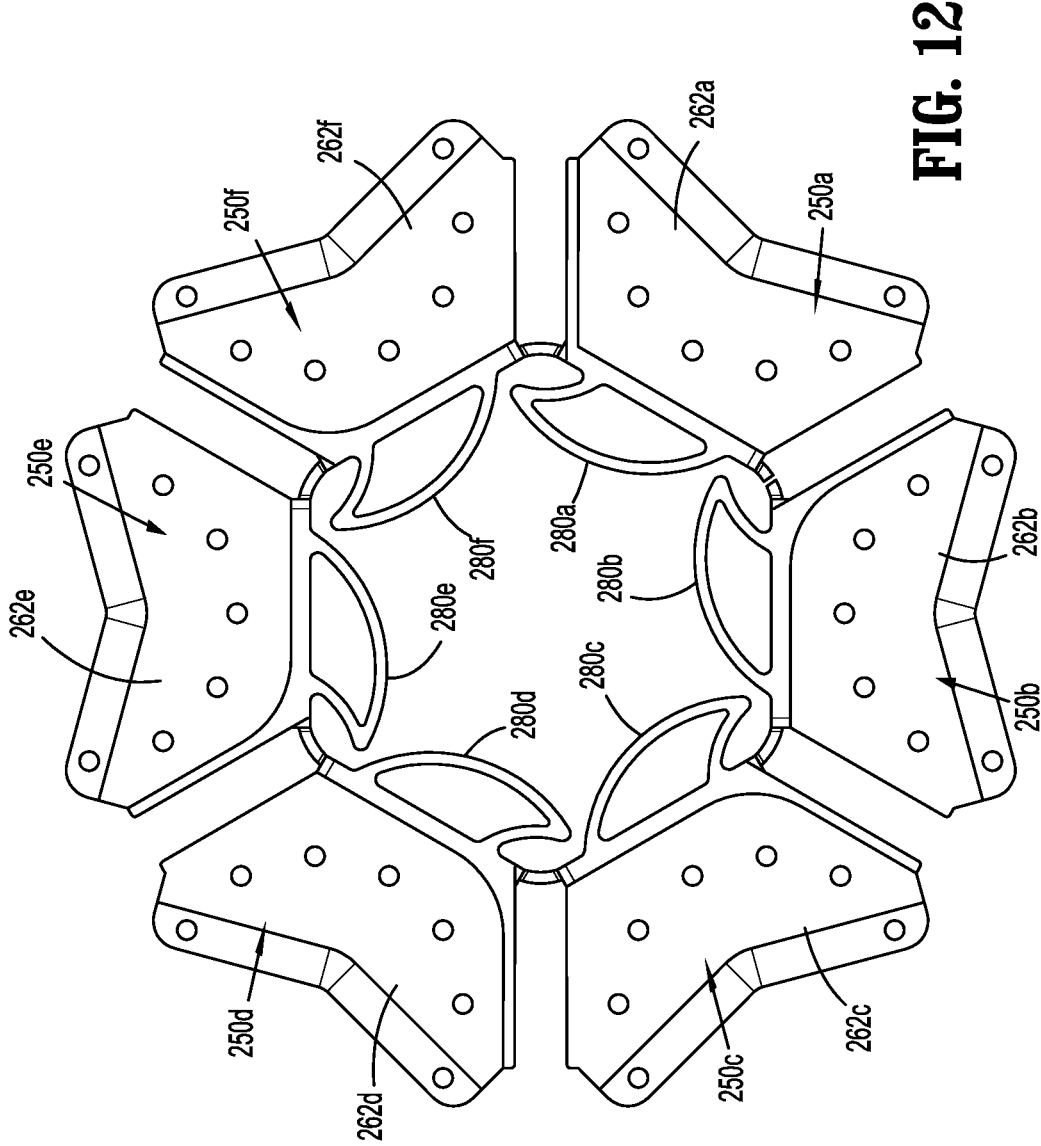
FIG. 12 is a top plan view of the instrument seal of FIG. 11 with a link severed.
Figure 14:
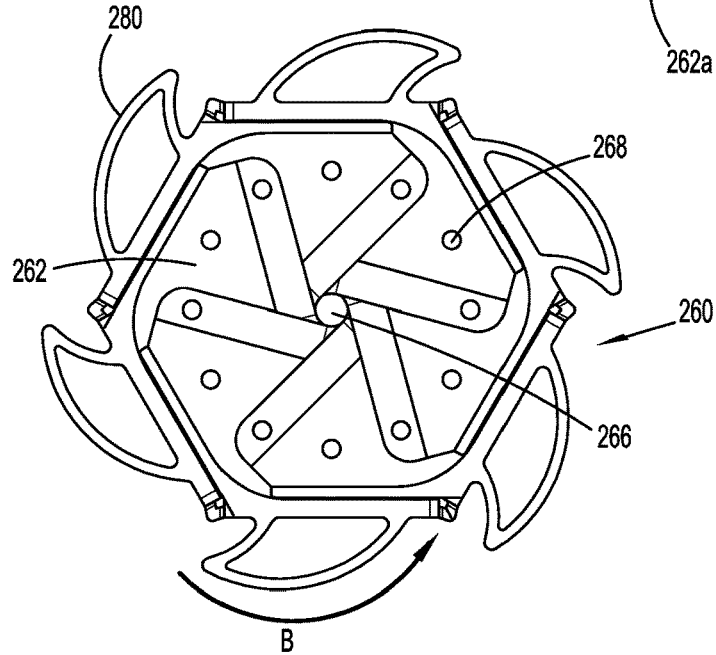
FIG. 14 is a top plan view of the instrument seal of FIG. 12 in a fully folded configuration illustrating the folding sequence of the petals.

With reference now to FIGS. 10-12, an alternate embodiment of an instrument seal is illustrated and identified generally as instrument seal 260. Instrument seal 260 may be a direct replacement for both the instrument seal 160 and the centering mechanism 130 in valve assembly 120 as illustrated in the previous embodiment. The instrument seal 260, as illustrated, includes a frame 270 having six sides 272a-f. The frame 270 may have fewer sides (e.g., 4) or more sides (e.g., 8). Each side 272a-f is generally rectangular and extends along a length of a corresponding petal 262a-f. The number of petals 262 is equal to the number of sides 272 of the frame 270. Links 278 extend between adjacent side 272 defining a plurality of living hinges. In particular, links 278 define living hinges between sides 272a-b, between sides 272b-c, between sides 272c-d, between sides 272d-e, and between sides 272e-f. A gap is defined between sides 272a and 272f allowing sides 272a and 272f to move relative to each other. This arrangement facilitates folding the seal 270 thereby transitioning the seal 270 from the unfolded or initial configuration as shown in FIG. 12 to the folded or final configuration as shown in FIG. 10. Since sides 272a and 272f have a gap therebetween and lack a living hinge, one of sides 272a or 272f may be repositioned without disturbing the position of the other of sides 272a or 272f. The instrument seal 260 also includes a plurality of fins 280a-f that extends from respective sides 272a-f on the side of the side 272a-f opposite that of the petals 262a-f. Each fin 280a-f is a flexible and resilient structure that is normally biased towards a center of the unfolded instrument seal 260 (FIG. 12) and normally biased away from the center of the folded instrument seal 260 (FIG. 14). The biasing and resilience of the fins 280a-f acts to center the instrument seal 260 when the instrument seal is positioned in the valve housing 110 (FIG. 15) as will be discussed in further detail hereinbelow.

Each petal 262a-f is a five sided main panel 250a-f with holes 268 extending therethrough. Although shown with five sides, each main panel 250a-f may have more or less than five sides. A first or connection side 261a-f is coupled to a side or segment 272a-f of the frame 270. In the unfolded configuration (FIGS. 11 and 12), each petal 262a-f extends away from an outer surface of the frame 270 outside a perimeter defined by the frame 270. In the folded configuration (FIGS. 10 and 14), each petal 262a-f is bounded by the frame 270 and is within the perimeter defined by the frame 270. Each main panel 250a-f has angled second and third sides 263a-f, 265a-f that extend from the connection side 261a-f in a divergent manner. Fourth and fifth sides 267a-f, 269a-f of main panels 250a-f interconnect the angled second and third sides 263a-f, 265a-f. The fourth and fifth sides 267a-f, 269a-f of the main panels 250a-f of each petal 262a-f have equal lengths and are angled towards the corresponding connection side 261a-f such that they meet a point that would bisect the connection side 261a-f. Additionally, the fourth and fifth sides 267a-f, 269a-f are oriented such that they define an angle between 120° and 160°. First and second extenders 264a-f, 266a-f are attached to the fourth and fifth sides 267a-f, 269a-f. Each extender 264a-f, 266a-f includes a hole 268 extending therethrough. The extenders 264a-f, 266a-f and the main panels 250a-f of each petal 262a-f bend at a midpoint between the second and third sides 263a-f, 265a-f of each petal 262a-f such that, when viewed from the end (i.e., from the extenders towards the connection side) (similar to FIG. 5), the petal 62a-f has a slight curvature of about 5° to about 10°.

Figure 13:
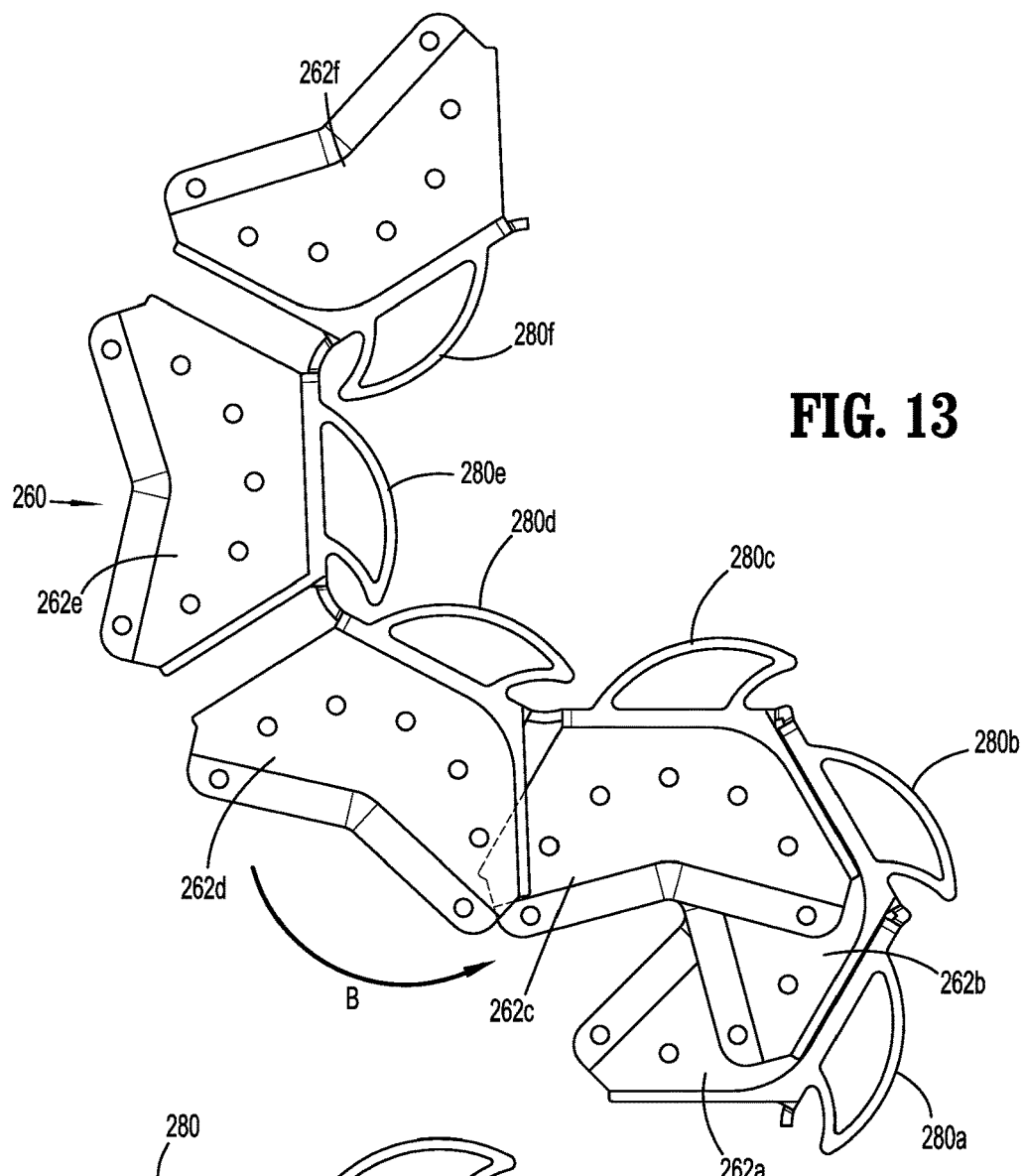
FIG. 13 is a top plan view of the instrument seal of FIG. 12 in a partially folded configuration illustrating the folding sequence of the petals.

The first petal 262a is folded by pivoting the first side 272a and the first petal 262a about the living hinge defined by the link 278 that is disposed between the first and second sides 272a, 272b in the direction of arrow "B". As such, the first petal 262a partially overlaps the second petal 262b. Subsequently, the first and second petals 262a, 262b are pivoted by pivoting the second side 272b about the living hinge defined by the link 278 that is disposed between the second side 272b and the third side 272c such that the second petal 262b partially overlaps the third petal 262c (FIG. 13). Next, the first, second, and third petals 262a-c are pivoted by pivoting the third side 272c about the living hinge defined by the link 278 that is disposed between the third side 272c and the fourth side 272d such that the third petal 262c partially overlaps the fourth petal 262d. Subsequently, the first, second, third, and fourth petals 262a-d are pivoted by pivoting the fourth side 272d about the living hinge defined by the link 278 that is disposed between the fourth side 272d and the fifth side 272e such that the fourth petal 262d partially overlaps the fifth petal 262e. The first, second, third, fourth, and fifth petals 262a-e are pivoted by pivoting the fifth side 272e about the living hinge defined by the link 278 that is disposed between the fifth side 272e and the sixth side 272f such that the fifth petal 262e partially overlaps the sixth petal 262f and the sixth petal 262f partially overlaps the first petal 262a. The fully folded seal 260 is illustrated in FIG. 14. All the folds occur in the direction identified by arrow "B".

After all the petals 262a-f are folded, a center orifice 266 is defined and is configured to engage an outer surface of a surgical instrument (not shown) inserted through the seal 260 such that the center orifice 266 surrounds the surgical instrument in a sealing manner to inhibit the passage of insufflation fluids and defines a fluid tight barrier. Further, once the petals 262a-f are folded over, the holes 268 of the petals 262a-f are aligned thereby allowing pins 186 of the retainer 180 to pass through the holes 268. In this embodiment, the pins 186 are insertable through bores 148 of the guard assembly 140, the holes 268 of the instrument seal, and the openings 188 of the second ring 184 of the retainer 180. This arrangement aligns the relative positions of the guard assembly 140 and the instrument seal 260. Although illustrated with pins 186 extending from the first ring 182 towards openings 188 in the second ring 184, the retainer may have the pins located on the second ring and the openings on the first ring. Alternatively, the first and second rings may have an alternating arrangement of pins and openings that are complementary such that the pins of one of the rings align with openings of the other of the rings allowing the rings to be attached to one another and define the retainer.

Figure 15:
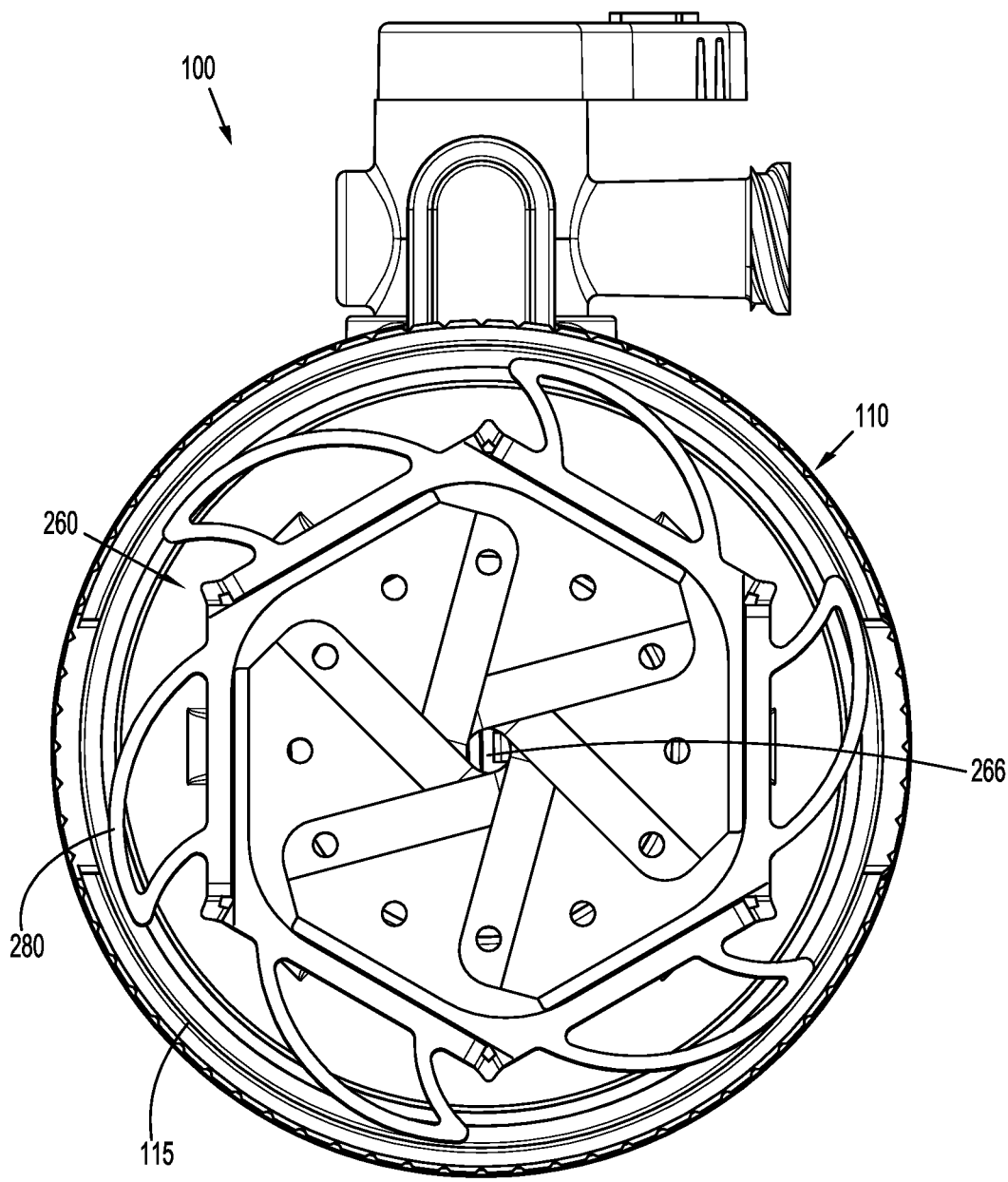
FIG. 15 is a top cross-sectional view of an instrument housing of the surgical access assembly taken along section line 15-15 of FIG. 1 showing the placement of the instrument seal of FIG. 10 disposed therein.

As each petal 262a-f at least partially overlaps a first adjacent petal 262 and is at least partially overlapped by a second adjacent petal 262, the petals 262a-f of the seal are interwoven. This interwoven arrangement of the petals 262a-f facilitates the seal 260 maintaining its shape during insertion and withdrawal of a surgical instrument through the center orifice 266. For example, with additional reference to FIG. 2, the seal 260 would replace the seal 160 and the centering mechanism 130. FIG. 15 illustrates the placement of the instrument seal 260 in vale housing 110 of the cannula assembly 100. During insertion of the surgical instrument through the valve housing 110 of the surgical access assembly 100, a shaft of the surgical instrument passes through the central opening 185 of the first ring 182, the central orifice 146 of the guard assembly 140, the center orifice 266 of the instrument seal 260, and the central opening 187 of the second ring 184. As the shaft of the surgical instrument passes through the center orifice 266 of the seal 260 during insertion, the petals 262a-f of the seal 260 flex towards the second ring 184 and surround an outer surface of the shaft of the surgical instrument providing a fluid tight barrier between the petals 262a-f of the seal 260 and the shaft of the surgical instrument. During withdrawal of the surgical instrument, the petals 262a-f of the seal 260 flex towards a proximal portion of the valve housing 110 in response to proximal movement of the shaft of the surgical instrument. The petals 262a-f of the seal 260 resiliently return to their initial or rest configuration (FIG. 10) once the shaft of the surgical instrument is removed from the center orifice 266 of the seal 260. Due to the petals 262a-f being interwoven, they return to their initial configuration. In the event that the petals 262a-f have slightly different rates of movement, the interwoven arrangement of the petals 262a-f results in the slowest moving petal 262 acting as a governor and limiting the rate of movement of the remaining petals 262. This tends to maintain contact between the petals 262a-f and the outer surface of the shaft of the surgical instrument thereby maintaining the fluid tight boundary of the seal 260 with respect to the surgical instrument during movement of the shaft relative to the seal 260.

Referring now to FIG. 15, the instrument seal 260 is positioned in the valve housing 110 and the fins 280a-f contact an inner wall 115 of the valve housing 110. In an initial state, the normal biasing force exerted by the fins 280a-f act to center the instrument seal 260 in the valve housing 110 such that the center orifice 266 is aligned with the central longitudinal axis "X" of the cannula assembly 100 (FIG. 2). When a surgical instrument is inserted through the valve housing 110 and the center orifice 266, any radial movement of the surgical instrument relative to the longitudinal axis "X" moves the instrument seal 260 in the same radial direction. This results in the center orifice 266 being radially offset from the central longitudinal axis "X". In particular, when the instrument seal 260 is moved radially, the fins 280a-f in the direction of movement are compressed more while the fins 280a-f on the opposing side a relaxed more. Thus, when the force is removed, the compressed fins 280a-f will move towards their initial position and return the instrument seal 260 to its at rest position where the center orifice 266 is aligned with the central longitudinal axis "X". It is contemplated that all of the fins 280a-f will be slightly compressed when the instrument seal 260 is disposed within the valve housing 110.

Each petal 262a-f is connected to a corresponding side 272a-f of the frame 270 along a first or connection side 261a-f. Each petal 262a-f also includes angled second and third sides 263a-f, 265a-f that extend from the corresponding connection side 261a-f in a divergent manner. Fourth and fifth sides 267a-f, 269a-f of each petal 262a-f interconnect the angled second and third sides 263a-f, 265a-f. The fourth and fifth sides 267a-f, 269a-f of the petals 262a-f have equal lengths and are angled towards the corresponding connection side 261a-f such that they meet at a point that would bisect the connection side 261a-f. The fourth and fifth sides are oriented such that they that they define an angle of 150°. The fourth and fifth sides may define an angle between about 120° and about 165°. First and second extenders 262a-f, 264a-f are attached to the fourth and fifth sides 267a-f, 269a-f. The first and second extenders 262a-f, 264a-f have equal lengths and meet at a taper 273a-f that also is located at a point that would bisect the corresponding connection side 261a-f.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A surgical access assembly comprising:
   a housing;
   a tubular member extending from the housing; and
   a valve assembly disposed in the housing, the valve assembly having:
   a centering mechanism having a central opening circumscribed by a lip having pores,
   a guard assembly having a central orifice alignable with the central opening of the centering mechanism and a ring having bores, the guard assembly disposed on a first side of the centering mechanism,
   an instrument seal including a polygonal frame and peripheral holes, the frame having a plurality of segments and a plurality of petals defining a central hole that is alignable with the central opening of the centering mechanism, the instrument seal disposed on a second side of the centering mechanism opposite the first side of the centering mechanism and proximate the tubular member, the plurality of petals arranged such that a portion of one petal of the plurality of petals covers a portion of a first adjacent petal of the plurality of petals and is covered by a portion of a second adjacent petal of the plurality of petals, each petal of the plurality of petals coupled to a corresponding segment of the plurality of segments and defining an acute angle with respect to a top surface of the corresponding segment of the plurality of segments, and a retainer having a first ring having pins disposed on the first side of the centering mechanism and a second ring having openings for receiving the pins disposed on the second side of the centering mechanism, the retainer sandwiching the centering mechanism between the first ring and the second ring, the pins of the first ring extending through the bores of the guard assembly, the pores of the centering mechanism, and the peripheral holes of the instrument seal to maintain the guard assembly, the centering mechanism, and the instrument seal in an aligned relationship.

2. The surgical access assembly of claim 1, wherein the pins of the first ring are received in the openings of the second ring.

3. The surgical access assembly of claim 1, wherein each petal of the plurality of petals is coupled to the corresponding segment of the plurality of segments with a living hinge.

4. The surgical access assembly of claim 1, wherein the centering mechanism includes a bellows.

5. A surgical access assembly comprising:
a housing;
a tubular member extending from the housing;
a valve assembly disposed in the housing, the valve assembly including:
a centering mechanism,
a guard assembly having a central orifice,
an instrument seal having a central hole aligned with the central orifice of the guard assembly, the instrument seal including a polygonal frame having a plurality of segments and a plurality of petals that are flexibly coupled to corresponding segments of the plurality of segments such that each petal of the plurality of petals defines an acute angle with respect to a top surface of the corresponding segment of the plurality of segments, the instrument seal having an unfolded configuration defined by the plurality of petals extending away from a center of the frame and a folded configuration defined by the plurality of petals folded towards the central hole of the instrument seal wherein each petal of the plurality of petals at least partially overlaps an adjacent petal of the plurality of petals such that the plurality of petals interlock, and
a retainer having a first ring disposed on a first side of the centering mechanism and a second ring disposed on a second side of the centering mechanism, the retainer sandwiching the centering mechanism between the first ring and the second ring to maintain the guard assembly, the centering mechanism, and the instrument seal in an aligned relationship.

6. The surgical access assembly of claim 5, wherein the folded configuration of the instrument seal defines a diameter of the central hole, the diameter configured to seal against a surgical instrument.

7. The surgical access assembly of claim 5, wherein each petal of the plurality of petals is flexibly coupled to the corresponding segment of the plurality of segments with a living hinge.

8. The surgical access assembly of claim 5, wherein the folded configuration of the instrument seal allows the plurality of petals to flex relative to the frame while the frame remains axially stationary relative to the housing.

9. The surgical access assembly of claim 5, wherein the centering mechanism has a central opening.

10. The surgical access assembly of claim 5, wherein the first ring of the retainer includes pins and the second ring of the retainer includes openings for receiving the pins, the pins of the first ring insertable through bores of the guard assembly, pores of the centering mechanism, and peripheral holes of the instrument seal to maintain the guard assembly, the centering mechanism, and the instrument seal in the aligned relationship.

11. The surgical access assembly of claim 5, wherein the centering mechanism includes a bellows.

12. A surgical access assembly comprising:
a housing;
a tubular member extending from the housing; and
a valve assembly disposed in the housing, the valve assembly having:
a centering mechanism having a central opening, and
an instrument seal in an abutting relationship with the centering mechanism, the instrument seal including a polygonal frame having a plurality of segments and a plurality of petals, a first end of each petal of the plurality of petals flexibly coupled to an outer surface of a corresponding segment of the plurality of segments of the frame and a second end of each petal of the plurality of petals repositionable between a first position where the second end is outside a perimeter of the frame and a second position where the second end is inside the perimeter of the frame, each petal of the plurality of petals partially overlapping an adjacent petal of the plurality of petals such that the plurality of petals interlock, each petal of the plurality of petals coupled to the corresponding segment of the plurality of segments of the frame at an acute angle relative to a top surface of the frame to facilitate interweaving the plurality of petals.

13. The surgical access assembly of claim 12, further including a central hole defined by the second position of the plurality of petals, the central hole defining a diameter configured to seal against a surgical instrument.

14. The surgical access assembly of claim 13, wherein the central hole of the instrument seal is alignable with the central opening of the centering mechanism.

15. The surgical access assembly of claim 12, further including first and second rings, the first ring disposed adjacent the centering mechanism and the second ring disposed adjacent the instrument seal, the centering mechanism and the instrument seal sandwiched between the first and second rings.

16. The surgical access assembly of claim 15, wherein the first ring includes pins extending from the first ring and the second ring includes openings for receiving the pins.

17. The surgical access assembly of claim 15, furthering including a guard assembly having a central orifice, the guard assembly disposed between the first ring and the centering mechanism.

* * * * *